United States Patent [19]

McGown

[11] Patent Number: 4,920,953
[45] Date of Patent: May 1, 1990

[54] DUAL CHANNEL CAP FOR ENDOSCOPE

[76] Inventor: George P. McGown, 21500 Johnson St., Box 523, Pembroke Pines, Fla. 33029-0523

[21] Appl. No.: 338,284

[22] Filed: Apr. 14, 1989

[51] Int. Cl.⁵ .............................................. A61B 1/00
[52] U.S. Cl. ...................................................... 128/4
[58] Field of Search ................................... 128/4, 4 A

[56] References Cited

U.S. PATENT DOCUMENTS 4,653,477  3/1987  Akui et al. ............................... 128/4
4,715,360  12/1987 Akui et al. ............................... 128/4
4,809,679  3/1989  Shimonaka et al. ..................... 128/4

OTHER PUBLICATIONS

Olympus Endoscopy Products Price List, Apr. 1, 1988.
Enclosed samples of Olympus channel caps, no date.

Primary Examiner—William H. Grieb
Attorney, Agent, or Firm—Jerry A. Miller

[57] ABSTRACT

An improved dual channel cap for use in conjunction with either a first or a second endoscopic channel valve or equivalent includes a main body portion having a first female opening suitable for mating with the first Olympus type endoscopic channel valve. A second female opening suitable for mating with the second Olympus type endoscopic channel valve is diametrically opposed to the first female opening. A slit couples the first female opening to the second female opening. A plug portion has a first male member suitable for mating with the first female opening. A second male member suitable for mating with the second female opening is diametrically opposed to the first male member. A first and a second channel passes through the first and second male members respectively, the first and second channels being coupled together with a slit. A strap connects the main body portion to the plug portion.

7 Claims, 1 Drawing Sheet

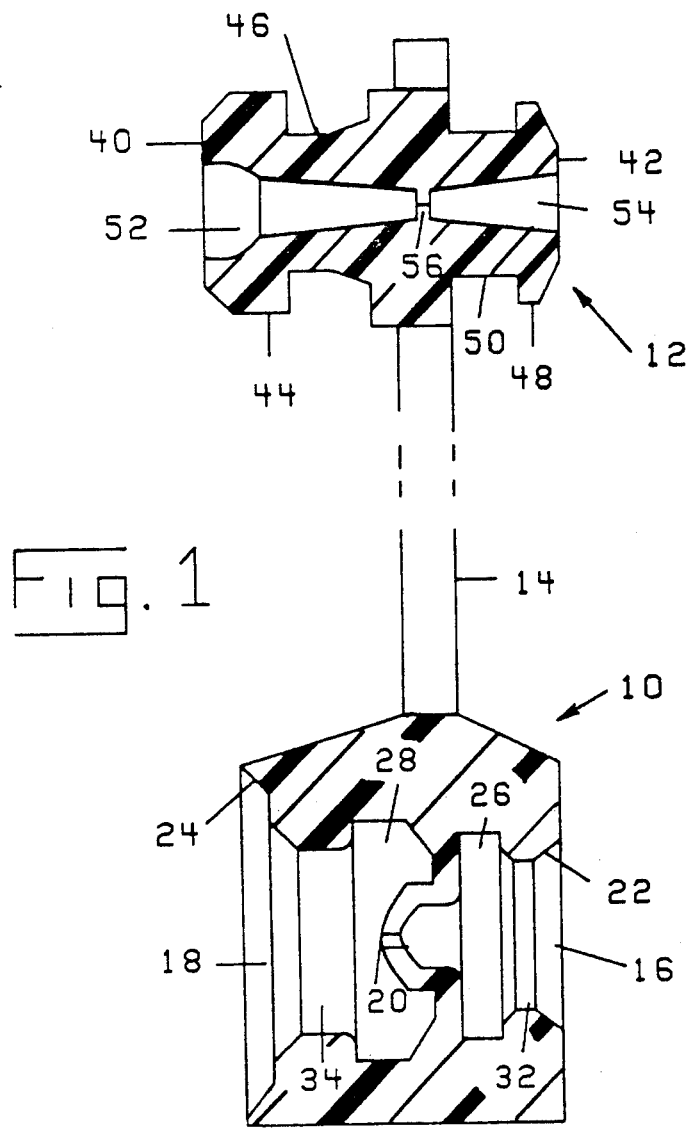

DUAL CHANNEL CAP FOR ENDOSCOPE

FIELD OF THE INVENTION

This invention relates generally to the field of flexible medical endoscopes. More particularly, this invention relates to an improved dual channel cap for providing enhanced sealing for improved suction effectiveness and the like. In particular, the present invention is well suited to flexible endoscopes manufactured by Olympus Corporation and equivalents thereof.

BACKGROUND OF THE INVENTION

Endoscopic products such as those manufactured by Olympus Corporation for use in operating rooms, outpatient surgery centers and gastrointestinal stations (as well as other non-medical uses) are fitted with a small semi-disposable channel cap (such as the Olympus MD-50 rubber cap, catalog No. 52888, or MB-348. catalog no. 52422) which fits over a channel valve. These products are available from Olympus Corporation, Medical Instrument Division, 4 Nevada Drive, Lake Success, N.Y. 11042. This channel cap has a slit through which forceps, suction tubes and other such medical instruments are passed and serves to provide a seal around such instruments. When suction is used, the seals should provide a good seal for the suction to be most effective.

In these instances, the standard channel caps are also provided with a plug portion attached to the main body of the channel cap by a strap. Many flexible instruments are routinely inserted and withdrawn through this channel cap. This plug portion, which also includes a slit passage therethrough, may be mated with the main body portion to provide a double seal through which the instruments may pass. Typically, such instruments may include various medical treatment instruments such as forceps and the like for taking biopsy samples, instruments for performing surgery, various tubes, and other such medical devices which pass through a diameter of approximately 1.5 to 3.7 mm.

These channel caps are typically used only a few times before the slit opens from wear to the point of providing an unacceptable seal. Consequently users may use a substantial number of these channel caps and in many cases must stock a substantial variety due to the various types and sizes of seals used for types and sizes of endoscopes (e.g. flexible fiber optic bronchoscope, gastroscope, colonoscope, etc.). Substantial problems have been noted in having the right size on hand when needed while maintaining a reasonable inventory of the parts. The present invention ameliorates these problems by providing a dual channel cap for different types, function and sizes of endoscopes as will as described below.

SUMMARY OF THE INVENTION

It is an object of the present invention to provide an improved channel cap for an endoscopic device.

It is another object of the present invention to provide an endoscopic channel cap capable of use with two sizes or types of channel valves.

It is a further object of the present invention to provide a channel cap which is compatible with the industry standard Olympus type endoscope products.

It is an advantage of the invention that fewer types of such channel caps must be maintained on hand, thus enhancing the economy of use of such channel caps, and it is easier to select an appropriate size channel cap.

These and other objects and advantages of the invention will become apparent to those skilled in the art upon consideration of the following description of the invention.

In one aspect of the present invention, an improved dual channel cap for use in conjunction with either a first or a second Olympus type flexible endoscopic channel valve or equivalent includes a main body portion having a first female opening suitable for mating with the first Olympus type endoscopic channel valve. A second female opening suitable for mating with the second Olympus type endoscopic channel valve is diametrically opposed to the first female opening. A slit couples the first female opening to the second female opening. A plug portion has a first male member suitable for mating with the first female opening. A second male member suitable for mating with the second female opening is diametrically opposed to the first male member. A first and a second channel passes through the first and second male members respectively, the first and second channels being coupled together with a narrow slit. A strap connects the main body portion to the plug portion.

In another aspect of the present invention, an improved dual channel cap for use in conjunction with either a first or a second flexible endoscopic channel valve, comprising a main body portion having a first female opening suitable for mating with the first endoscopic channel valve, and having a second female opening suitable for mating with the second endoscopic channel valve, the first and second female openings may be diametrically opposed. A channel couples the first female opening to the second female opening. A plug portion has a first male member suitable for mating with the first female opening, and a second male member suitable for mating with the second female opening. A strap connects the main body portion to the plug portion.

The features of the invention believed to be novel are set forth with particularity in the appended claims. The invention itself, however, both as to organization and method of operation, together with further objects and advantages thereof, may be best understood by reference to the following description taken in conjunction with the accompanying drawing.

BRIEF DESCRIPTION OF THE DRAWING

FIG. 1 shows a cross-sectional drawing of one embodiment of a dual channel cap of the present invention.

DETAILED DESCRIPTION OF THE INVENTION

Turning now to FIG. 1, a dual channel cap of the present invention is shown in cross-section. Those skilled in the art will appreciate that many variations and combinations of sizes and configurations may be possible within the scope of the present invention. The dual channel cap of FIG. 1 includes a main body portion 10 and a plug portion 12 which are connected together by an integral connecting portion referred to herein as a strap 14. The entire device is molded from a soft rubber or elastic-like material such as that used to manufacture conventional single channel caps such as that shown in U.S. Pat. No. 4,809,679 which is incorporated by reference.

The main body portion 10 includes a first female opening 16 which is appropriately shaped to mate with a first predetermined channel valve or the like. Diametrically opposed to the first female opening 16 is a second female opening 18 suitably shaped to mate with a second predetermined channel valve or the like. Those skilled in the art may recognize alternatives to the placement of the two female openings in diametric opposition. The present invention contemplates such alternatives.

The respective female openings may be shaped and sized to adapt to two different size channel valves, or may be shaped and sized to accommodate two different types of channel valves or the like. In the embodiment shown in FIG. 1, the respective female openings are designed to mate with two different types of channel valves, but this is not to be limiting.

The two female openings 16 and 18 are coupled together by an opening 20 which is preferably a slit which may be cut as a secondary manufacturing operation. This opening should be only large enough to pass the typical 1.5 to 3.7 mm instruments used in conjunction with conventional flexible endoscopes according to the preferred embodiment, however, appropriate scaling for other embodiments is within the scope of the present invention. The outer portions 22 and 24 respectively of female openings 16 and 18 respectively are preferably tapered to facilitate installation of the channel cap, or plugging of the channel as desired. The innermost chambers 26 and 28 of the female openings 16 and 18 respectively are typically larger in diameter than central areas 32 and 34 respectively to firmly hold the channel valve opening or plug portion.

In use, either one of female openings 16 or 18 may be mated to an appropriate channel valve as required. This is accomplished in a conventional manner by simply pressing the female opening firmly against the male portion of the channel valve until the flexible rubber channel cap snaps into engagement. When it is desired to plug the main body 10 of the channel cap to obtain a seal, the plug portion is used. In the event a channel valve is mated to female opening 16, a male member 40 is mated to female opening 18. In the event a channel valve or the like is mated to female opening 18, a male member 42 is mated to female opening 16. Mating of the male member 40 or 42 with the female opening 18 or 16 is accomplished in the same manner as above-described for mating the channel valve with the female openings.

In essence, the male members 40 and 42 of plug portion 12 are designed to mate with whatever female configuration is present at female openings 16 and 18 of main body 10. In the embodiment shown in FIG. 1, male member 40 includes a wider diameter outer portion 44 which is tapered at the outermost part to facilitate ease of the insertion into the female opening 18 and will snap into engagement with the larger diameter portion 28. A narrower neck 46 rests within the central portion 34 when engaged.

In a similar manner, a wider outermost portion 48 of male member 42 (also tapered at the outermost part to facilitate insertion) is designed to mate within the larger diameter chamber 26 of female opening 16. A central neck 50 rests within the central portion 32 when engaged.

A channel 52 is provided in male member 40 and a similar channel 54 is provided in male member 42. The channels 52 and 54 may be coupled together if desired by a slit 56 through which suction tubes, forceps, fiberoptics and the like may pass.

Thus, when the plug portion 12 is mated (in either configuration) with the main body portion 10, a more or less conventional dual seal familiar to users of such equipment is provided. However, the present invention allows a single such channel cap to be stocked for use with two different channel valves.

Thus it is apparent that in accordance with the present invention, an improved apparatus and method that fully satisfies the objectives, aims and advantages is set forth above. While the invention has been described in conjunction with specific embodiments, it is evident that many alternatives, variations, modifications and permutations will become apparent to those skilled in the art in light of the foregoing description. Accordingly, it is intended that the present invention embrace all such alternatives, variations, modifications and permutations as fall within the spirit and broad scope of the appended claims.

What is claimed as new and desired to be secured by Letters Patent is:

1. An improved dual channel cap for use in conjunction with either a first or a second endoscopic channel valve, comprising:
    a main body portion having a first female opening suitable for mating with said first endoscopic channel valve, and having a second female opening suitable for mating with said second endoscopic channel valve;
    a channel coupling said first female opening to said second female opening;
    a plug portion having a first male member suitable for mating with said first female opening, and a second male member suitable for mating with said second female opening; and
    a strap connecting said main body portion to said plug portion.

2. The apparatus of claim 1, wherein said first and second female openings are approximately diametrically opposed.

3. The apparatus of claim 1, wherein said channel comprises a slit.

4. The device of claim 1, further comprising a channel coupling said first male member to said second male member.

5. An improved dual channel cap for use in conjunction with either a first or a second endoscopic channel valve, comprising:
    a main body portion having a first female opening suitable for mating with said first endoscopic channel valve, and having a second female opening suitable for mating with said second endoscopic channel valve, said first and second female openings being diametrically opposed;
    a slit coupling said first female opening to said second female opening;
    a plug portion having a first male member suitable for mating with said first female opening, and a second male member suitable for mating with said second female opening, said first and second male members being diametrically opposed;
    a first and a second channel passing through said first and second male members respectively, said first and second channels being coupled together with a narrow slit; and
    a strap connecting said main body portion to said plug portion.

6. An improved dual channel cap for use in conjunction with either a first or a second endoscopic channel valve, comprising:

main body means having a first female opening suitable for mating with said first endoscopic channel valve, and having a second female opening suitable for mating with said second endoscopic channel valve;

means for coupling said first female opening to said second female opening;

plug means having a first male member suitable for mating with said first female opening, and a second male member suitable for mating with said second female opening; and connecting means for connecting said main body portion to said plug portion.

7. The apparatus of claim 6, wherein said connecting means includes a strap.

* * * * *